United States Patent [19]

Fujiwara et al.

[11] 4,379,842

[45] Apr. 12, 1983

[54] PROCESS FOR THE MANUFACTURE OF 1α-HYDROXYDEHYDROEPIANDROSTERONE

[75] Inventors: Akiko Fujiwara, Kamakura; Chikara Miyamoto, Yokohama; Toru Okuda, Yakuoji, all of Japan

[73] Assignee: Hoffmann-La Roche Inc., Nutley, N.J.

[21] Appl. No.: 295,281

[22] Filed: Aug. 24, 1981

Related U.S. Application Data

[63] Continuation of Ser. No. 121,120, Feb. 13, 1980.

[51] Int. Cl.³ .................... C12P 33/06; C12R 1/80; C12R 1/66
[52] U.S. Cl. .................... 435/58; 435/933; 435/913
[58] Field of Search ...................................... 435/58

[56] References Cited

U.S. PATENT DOCUMENTS 2,805,231  9/1957  Dodson et al. .................... 435/58
2,833,793  5/1958  Dodson et al.
2,833,794  5/1958  Goldkamp et al. .................... 435/58
4,144,334  3/1979  Petzoldt et al. .................... 435/58

FOREIGN PATENT DOCUMENTS 809494  2/1959  United Kingdom .

OTHER PUBLICATIONS

J. Amer. Chem. Soc., vol. 79, p. 3921 (1957).

*Primary Examiner*—Alvin E. Tanenholtz
*Attorney, Agent, or Firm*—Jon S. Saxe; George M. Gould; Peter R. Shearer

[57] ABSTRACT

The invention relates to a process for producing 1α-hydroxydehydroepiandrosterone by fermenting or reacting dehydroepiandrosterone or a derivative thereof with microorganisms of the species *Penicillium oxalicum* or *Aspergillus terreus* or mycelium or extracts therefrom obtained when the microorganisms are in a stationary phase of growth. The invention process produces steroid compounds which are pharmacologically valuable substances.

9 Claims, No Drawings

4,379,842

PROCESS FOR THE MANUFACTURE OF 1α-HYDROXYDEHYDROEPIANDROSTERONE

This is a continuation of application Ser. No. 121,120 filed Feb. 13, 1980.

BACKGROUND OF THE INVENTION

The Japanese patent application Kokai No. 63990/1976 discloses the manufacture of 1α,17β-dihydroxy-steroids by 1α-hydroxylation of 17β-hydroxy-17α-substituted or unsubstituted 4-oestren-3-ones by means of microorganisms of the genus Rhizoctonia, Calonectria, Glomerella, Aspergillus, Corticium, Septomyxa, Mucor, Isaria, Irpex or Fusarium. All of these organisms, with the exception of the species Aspergillus terreus, are not in the position to hydroxylate dehydroepiandrosterone in the 1α-position. This fact means that a 1α-hydroxylation of steroids can be carried out only with quite specific combinations of microorganisms and substrates. It is, indeed, very difficult to discover such a combination. According to the process of the above-mentioned patent application, Aspergillus clavatus ATCC 9598, A. fumigatus mut. helvola CBS 110.46 and A. conicus IFO 4047 are microorganisms which can hydroxylate in the 1α-position steroids with an oxo group in the 3-position, a double-bond in the 4,5-position and a hydroxy group in the 17β-position. These aforementioned microorganisms can not, however, hydroxylate in the 1α-position dehydroepiandrosterone or derivatives thereof which have in the 3-position a hydroxy group, 5,6-double bond and a 17-oxo group.

U.S. Pat. No. 2,882,794 discloses a process for the hydroxylation of dehydroisoandrosterone (dehydroepiandrosterone) in the 1α-position by means of Penicillium sp. ATCC 12556. This process has the disadvantage that substrate concentrations, namely 0.35 g/l, must be employed. It is difficult to manufacture 1α-hydroxy-dehydroepiandrosterone in high yield according to the procedure described in the above U.S. Patent. Furthermore when low substrate concentrations are used the hydroxylation product appears to decompose immediately after reaching the highest yield.

SUMMARY OF THE INVENTION

A process for producing 1α-hydroxydehydroepiandrosterone by combining dehydroepiandrosterone or derivatives thereof with Penicillium oxalicum or Aspergillus terreus in stationary growth phase or mycelium or extracts therefrom. The invention process produces steroid compounds which are intermediates for the manufacture of pharmacologically valuable substances and which themselves exhibit pharmacological (e.g. hormonal) activity.

DETAILED DESCRIPTION OF THE INVENTION

The present invention relates to a process for producing in high yield 1α-hydroxydehydroepiandrosterone by adding dehydroepiandrosterone or a derivative thereof as a substrate for 1α-hydroxylation to microorganisms of the species Penicillium oxalicum or Aspergillus terreus fermenting in a culture medium, the addition of the substrate being made at a time when the microorganisms are in a stationary phase of growth.

The present invention also relates to a process for producing in high yield 1α-hydroxydehydroepiandrosterone by reacting dehydroepiandrosterone or a derivative thereof as a substrate with mycelium isolated from a culture of microorganism of the species Penicillium oxalicum or Aspergillus terreus, the isolation being made at a time when the microorganisms are in a stationary phase of growth.

Furthermore the present invention relates to a process for producing in high yield 1α-hydroxydehydroepiandrosterone by reacting dehydroepiandrosterone or a derivative thereof as a substrate with enzyme extract manufactured from microorganisms of the species Penicillium oxalicum or Aspergillus terreus at a time when the microorganisms are in a stationary phase of growth.

Any strain of microorganisms of the species Penicillium oxalicum or Aspergillus terreus that are capable of 1α-hydroxylation of dehydroepinadrosterone or a derivative thereof can be used in the invention process. Preferred strains are Penicillium oxalicum IFO-5748 (FERM-P No. 4727), P. oxalicum IFO-6579 (FERM-P No. 4728), P. oxalicum IFO-7000 (FERM-P No. 4729), P. oxalicum IFO-7085 (FERM-P No. 4730), Aspergillus terreus IFO-6123 (FERM-P No. 4726) and variants thereof. The notation FERM-P relates to cultures of the Fermentation Research Institute, Chiba City, Japan; IFO denotes the Institute for Fermentation, Osaka, Japan.

The following strains of the genus Penicillium and Aspergillus can not hydroxylate dehydroepiandrosterone or a derivative thereof: P. verruculosum, P. notatum, P. chrysogenum, P. decumbens, P. fellutanum. P. frequentans, P. purpurrescens, P. terlikowskii, P. lilacino-echinulatum. P. multicolor, P. simplicissimum, P. herquei, P. implicatum, P. janthinellum, P. charlessi, P. citreo-viride, P. corylophiloides, P. cyaneum, P. adametzi, P. aeneum, P. thomii, and P. sclerotiorum: A. flavus, A. ustus, A. clavatus, A. parasiticus, A. conicus, A. carneus and A. fumigatus.

In the culivation of the microorganism, a suitable culture medium can be inoculated with the microorganism. Suitable culture media are such ones which contain carbon sources, nitrogen sources, inorganic salts and other nutrient substances permitting the growth of the microorganism. The preferred carbon sources, are, for example, glucose, sucrose, dextrin, mannose, starch, lactose and glycerine; nitrogen sources are, for example, nitrogen-containing organic substances such as peptone, meat extract, yeast extract, cornsteep liquor and casein, or nitrogen-containing inorganic compounds such as nitrates and inorganic ammonium salts; organic salt sources are, for example, phosphates or sodium, potassium, magnesium, manganese, iron and copper salts. The microorganism can be submersed in the culture, as by shaking the culture, or the microorganism may be cultivated in a stationary culture. The microorganism is preferably cultivated under aerobic conditions. Any art recognized procedure for cultivating the microorganism may be used.

The invention process may be conveniently carried out by adding dehydroepiandrosterone or a derivative thereof as a substrate to the cultivated microorganisms in the culture medium. The concentration of the substrate is not particularly significant but a concentration of 1 to 15 grams per liter is preferred. The most preferable concentration is 1 to 10 grams per liter. The 1α-hydroxylation in accordance with the invention process can be carried out by continuation of the cultivation of the microorganism under the above mentioned conditions in the presence of the substrate to be 1α-hydroxylated. The fermentation or cultivation time needed for significant hydroxylation can vary depending on species and strain of the microorganism used, on the composition of the culture medium, on the substrate used and on the concentration of substrate and microorganism. In general, a fermentation time of 1–10 days suffices. The fermentation temperature preferred generally lies between 20° and 30° C., and a preferable pH between 4–9.

The point in time of the addition of the substrate to the microorganisms or mycelium or of the manufacture of the enzyme extract from the microorganisms or mycelium for reaction with the substrate is important in order to obtain a high yield of 1α-hydroxydehydroepiandrosterone in the invention process. The addition of the substrate for the manufacture of the enzyme extract must take place when the microorganisms are in a stationary phase of growth. The stationary phase of growth contemplated is the phase at which a required nutrient of the culture medium becomes limited. More particularly the stationary phase of growth contemplated is the phase at which the carbon source is almost completely consumed.

The point in time at which the carbon source in the culture medium or nutrient solution is almost completely consumed can be established e.g. by determination of the glucose content of the culture medium. The addition of the substrate, for example, can be effected e.g. when the glucose content of the culture medium has dropped to 0.05 to 0.02%. Since the growth of the microorganism stagnates when the carbon source is consumed, the point in time of the substrate addition can also be ascertained by observing the change of the cell mass of the microorganisms per volume unit (e.g. g dry cells/liter of fermentation solution). The substrate is conveniently added when the dry cell weight per volume unit no longer increases. This point in time depends on the fermentation conditions and can be reached e.g. after 2 days.

Dehydroepiandrosterone or various art recognized pharmacologically active derivatives of dehydroepiandrosterone may be employed as the substrate in this invention process. Among the derivatives that may be employed as substrate are included the 3-acyl derivatives. Among the preferred 3-acyl derivatives are the 3-lower alkanoyl derivatives. An especially preferred derivative is dehydro epiandrosterone-3-acetate. Other 3-acyl derivatives which can be used in accordance with this invention include 3-benzoyl derivatives. The term lower alkanoyl designates lower alkanoyl substituents having from 1 to 7 carbon atoms such as formyl, acetyl, propionyl, butyryl, tert.butyryl and the like.

The substrate, dehydroepiandrosterone or a derivative thereof, can be added or reacted in the form of a fine powder or in the form of a solution in a hydrophilic solvent such as acetone, dimethyl sulphoxide, methanol, ethanol, ethyleneglycol, propyleneglycol or dioxan. A surface active or dispersion agent can also be added to an aqueous suspension of the substrate or the substrate can be emulsified by treatment with ultrasonic wave.

When the invention is carried out with the mycelium isolated from the culture medium of the microorganism or with an enzyme extract manufactured in a manner known per se from the culture medium or the mycelium, the 1α-hydroxylation is conveniently performed in solution, e.g. in a buffer solution, in a physiological salt solution, in fresh nutrient solution or in water.

The product (the 1α-hydroxylated steroid) can be isolated from the culture medium or fermentation mixture by any process recognized in the art for this purpose, as for example, by solvent extraction with an organic solvent which is not miscible with water, such as chloroform, methylene chloride or ethyl acetate or by chromatography on carriers such as aluminum oxide, silica gel or cellulose. The isolated product can also be purified by recrystallization, e.g. from methanol, ethanol, ethyl acetate, benzene or acetone.

The preferred strains of microorganisms used according to the present invention, namely Penicillium oxalicum IFO-5748 (FERM-P No. 4727), *P. oxalicum* IFO-6579 (FERM-P No. 4728), *P. oxalicum* IFO-7000 (FERM-P No. 4729), *P. oxalicum* IFO-7085 (FERM-P No. 4730), *Aspergillus terreus* IFO-6123 (FERM-P No. 4726) have been deposited at the American Type Culture Collection, Rockeville, Md. under ATCC Nos. 20,590; 20,591; 20,592; 20,593; and 20,589, respectively The 1α-hydroxylated steroid, namely, 1α-hydroxydihydroepiandrosterone, is a known compound which can be employed as an intermediate by any art recognized procedure for producing synthetic hormones and various pharmaceuticals.

The following Examples illustrate the invention process but are not meant to limit the invention in scope or spirit. The temperatures are given in degrees Centigrade.

EXAMPLE 1

A 500 ml flask with 100 ml of a medium containing 1% glucose and 1% cornsteep liquor was autoclaved at 120° for 20 minutes. The pH of the medium was previously adjusted to 6.5. After cooling down, the flask content was inoculated with spores of an agar slant culture of Penicillium oxalicum IFO-7000 (FERM-P No. 4729).

The flask was then incubated at 26.5° for 2 days on a rotary shaking machine. Dehydroepiandrosterone was suspended in a 0.1% Tween 80 solution under ultrasonication and added to the flask content up to an end concentration of 5 g/l. The incubation was continued 3 days under the above conditions.

10 ml samples were removed and extracted while shaking with three parts by volume of ethyl acetate. A portion of the extract was analysed by thin-layer chromatographically with silica gel plates and a solvent system of chloroform-acetone (2:1) and cyclohexane-toluene-ethanol (8:2:2.5), as well as by gas-liquid chromatography. The yield of 1α-hydroxydehydroepiandrosterone amounted to 45.0%.

EXAMPLE 2

Following the procedure of Example 1, 1α-Hydroxydehydroepiandrosterone was obtained in 30.2% yield with the substrate being added as a powder in an end concentration of 5 g/l.

EXAMPLE 3

Following the procedure of Example 1, 1α-Hydroxydehydroepiandrosterone was obtained in yields of 36.3% and 26.5% with substrate concentrations of 3 g/l and 7 g/l, respectively.

EXAMPLE 4

Following the procedure in Example 1, 1α-Hydroxydehydroepiandrosterone was obtained in 32% yield with a substrate concentration of 3 g/l of dehydroepiandrosterone-3-acetate.

EXAMPLE 5

Following the procedure in Example 1, 1α-Hydroxydehydroepiandrosterone was obtained in yields of 24.0%, 23.2% and 32.0% with the use of Penicillium oxalicum IFO-5748 (FERM-P No. 4727), IFO-6579 (FERM-P No. 4728) and IFO-7085 (FERM-P No. 4730), respectively.

EXAMPLE 6

A 500 ml flask with 100 ml of a medium containing 1% glucose and 1% cornsteep liquor was inoculated with spores of Aspergillus terreus IFO-6123 (FERM-P No. 4726) and shaken at 26.5° for 2 days. 100 ml of dehydroepiandrosterone were suspended in 2 ml of 0.1% Tween 80 solution under ultrasonication and added to the content of the flask. The cultivation was continued for 2 days, whereupon 1α-hydroxydehydroepiandrosterone was isolated from the medium and identified.

EXAMPLE 7

A 500 ml flask with 100 ml of pre-sterilised medium (pH 6.5) containing 1% glucose and 1% cornsteep liquor was inoculated with a slant culture of Penicillium oxalicum IFO-7000 (FERM-P No. 4729) and shaken at 26.5° for 2 days. A 5 l fermentation vessel with 3 liters of pre-sterilised medium was inoculated with the thus-obtained culture. The fermentation was continued for 37 hours and at 26.5° with stirring (300 rpm) and aeration (1 v/v).

A suspension of 15 g of dehydroepiandrosterone in 300 ml of 0.1% Tween 80 was exposed to ultrasonic wave for 10 minutes and added to the fermentation vessel. The fermentation was continued for 79 hours under the above conditions. The production of 1α-hydroxydehydroepiandrosterone in the nutrient medium amounted to 5.36 g.

The culture was harvested, extracted with 3 liters of ethyl acetate and the mycelium was filtered off. The aqueous acetone extract of the mycelium was concentrated for the removal of the acetone and extracted with ethyl acetate. The aqueous phase of the first extraction was likewise extracted with ethyl acetate. The combined extracts were concentrated to a small volume under reduced pressure. 3.82 g of solid were filtered off. Crystallisation of the solid from a mixture of methanol and ethyl acetate yielded 2.56 g of pure 1α-hydroxydehydroepiandrosterone of melting point ca 279°.

The mother liquor from the filtration and the crystallisation was evaporated to dryness and chromatographed on a silica gel column. The column was eluted with a mixture of acetone and chloroform. During the elution the proportions of acetone were gradually increased. There were thus obtained 1.5 g of 1α-hydroxydehydroepiandrosterone of melting point 278.5°.

EXAMPLE 8

Ten 500 ml flasks each containing 100 ml of nutrient medium (1% glucose, 1% cornsteep liquor, pH 6.5) were inoculated with spores of a slant culture of Penicillium oxalicum IFO-7000 (FERM-P No. 4729) and cultivated while shaking at 26.5° for 2 days. The mycelium was collected by filtration, and washed with sterile water. The washed mycelium was added to a 5 liter flask containing 1 liter of 0.85% salt solution, 10 g of CaCO₃ and 1 g of dehydroepiandrosterone. The flask was incubated at 26.5° for 20 hours with shaking. After that, 35% of the dehydroepiandrosterone had been converted into the corresponding 1α-hydroxy compound. The reaction mixture was extracted with 1 liter of ethyl acetate and the mycelium was filtered off. The organic phase was dried over sodium sulphate and concentrated to a solid which was then added to a silica gel column. The column was eluted with chloroform and a mixture of acetone and chloroform, during the elution the acetone proportion being gradually increased to a ratio of 5:95 (acetone:chloroform). There were thus obtained 230 mg of pure 1α-hydroxydehydroepiandrosterone of melting point 278,5°.

What is claimed is:

1. A process for producing 1-α-hydroxydehydroepiandrosterone comprising adding dehydroepiandrosterone or 3-acyldehydroepiandrosterone as a substrate to microorganisms of the species Penicillium oxalicum or Aspergillus terreus fermenting in a culture medium, the addition of substrate being made at a time when the microoganisms are in a stationary phase of growth and for a time sufficient for conversion of the substrate.

2. A process for producing 1-α-hydroxy dehydroepiandrosterone comprising reacting dehydroepiandrosterone or 3-acyl-dehydroepiandrosterone as a substrate with mycelium isolated from a culture of microorganisms of the species Penicillium oxalicum or Aspegillus terreus, the isolation being made at a time when the microorganisms are in a stationary phase of growth and the substrate reacting for a time sufficient for conversion of the substrate.

3. A process according to claim 1, wherein the microorganism is *Penicillium oxalicum* IFO-5748 (FERM-P No. 4727), *Penicillium oxalicum* IFO-6579 (FERM-P No. 4728), *Penicillium oxalicum* IFO-7000 (FERM-P No. 4729), *Penicillium oxalicum* IFO-7085 (FERM-P No. 4730) or *Aspergillus terreus* IFO-6123 (FERM-P No. 4726).

4. A process according to claim 1 wherein the substrate is dehydroepiandrosterone-3-acetate.

5. A process according to claim 2, wherein the microorganism is *Penicillium oxalicum* IFO-5748 (FERM-P No. 4727), *Penicillium oxalicum* IFO-6579 (FERM-P No. 4728), *Penicillium oxalicum* IFO-7000 (FERM-P No. 4729), *Penicillium oxalicum* IFO-7085 (FERM-P No. 4730) or *Aspergillus terreus* IFO-6123 (FERM-P No. 4726).

6. A process according to claim 2, wherein the substrate is dehydroepiandrosterone-3-acetate.

7. A process for producing 1-α-dehydroxyepiandrosterone comprising reacting dehydroepiandrosterone or 3-acyl-dehydroepiandrosterone as a substrate to microorganisms of the species *Penicillium oxalicum* or *Aspergillus terreus* fermenting in a culture medium, said substrate being in a concentration of 1–15 grams per liter of medium and being added at a time when the microorganisms are in a stationary phase of growth and for a time sufficient for conversion of the substrate.

8. A process according to claim 8 wherein the microorganism is *Penicillium Oxalicum* IFO-5748 (FERM-P No. 4727), *Penicillium oxalicum* IFO-6579 (FERM-P No. 4728), *Penicillium oxalicum* ISO-7000 (FERM-P No. 4729), *Penicillium oxalicum* IFO-7085 (FERM-P No. 4730) or *Aspergillus terreus* IFO-6123 (FERM-P No. 4726).

9. A process according to claim 8 wherein the substrate is dehydroepiandrosterone-3-acetate.

* * * * *